(12) United States Patent
Lee et al.

(10) Patent No.: US 10,888,303 B2
(45) Date of Patent: Jan. 12, 2021

(54) METHOD AND ULTRASOUND SYSTEM FOR FORMING CONTRAST PULSE SEQUENCE ULTRASOUND IMAGE

(71) Applicant: Siemens Medical Solutions USA, Inc., Malvern, PA (US)

(72) Inventors: SangSin Lee, Seongnam-si (KR); DongYoung Choi, Seoul (KR)

(73) Assignee: Siemens Medical Solutions USA, Inc., Malvern, PA (US)

( * ) Notice: Subject to any disclaimer, the term of this patent is extended or adjusted under 35 U.S.C. 154(b) by 404 days.

(21) Appl. No.: 15/687,135

(22) Filed: Aug. 25, 2017

(65) Prior Publication Data

US 2018/0085092 A1 Mar. 29, 2018

(30) Foreign Application Priority Data

Sep. 27, 2016 (KR) .............................. 2016-0124055

(51) Int. Cl.
*A61B 8/08* (2006.01)
*G01S 15/89* (2006.01)
*A61B 8/00* (2006.01)
*A61B 8/14* (2006.01)

(52) U.S. Cl.
CPC .............. *A61B 8/5207* (2013.01); *A61B 8/14* (2013.01); *A61B 8/461* (2013.01); *A61B 8/467* (2013.01); *A61B 8/481* (2013.01); *A61B 8/54* (2013.01); *G01S 15/89* (2013.01)

(58) Field of Classification Search
CPC ......... A61B 8/5207; A61B 8/54; A61B 8/481; A61B 8/467; A61B 8/461; A61B 8/14; A61B 8/52; A61B 8/4483
See application file for complete search history.

(56) References Cited

U.S. PATENT DOCUMENTS

| | | | |
|---|---|---|---|
| 6,494,841 B1 | 12/2002 | Thomas et al. | |
| 6,632,177 B1 | 10/2003 | Phillips et al. | |
| 7,004,906 B1 | 2/2006 | Guracar | |
| 7,591,788 B2 | 9/2009 | Phillips et al. | |
| 7,713,209 B2 | 5/2010 | Guracar | |
| 2002/0002333 A1* | 1/2002 | Angelsen | G01S 7/52038 600/443 |

(Continued)

*Primary Examiner* — Katherine L Fernandez
*Assistant Examiner* — Michael S Kellogg (57) ABSTRACT

A method for forming a contrast pulse sequence ultrasound image using a pulse width modulation scheme and an ultrasound system using the same are disclosed. The ultrasound system generates at least three kinds of mutually different pulses having a same amplitude, and sequentially transmits at least three kinds of transmission signals corresponding to the at least three kinds of mutually different pulses to an ultrasound transducer. The ultrasound transducer transmits at least three kinds of ultrasound signals to a target object by sequentially generating the at least three kinds of ultrasound signals based on the at least three kinds of transmission signals. The ultrasound transducer generates at least three kinds of reception signals by sequentially receiving at least three kinds of echo signals reflected from the target object. The ultrasound system forms a contrast pulse sequence ultrasound image by eliminating a linear component from the at least three kinds of reception signals.

10 Claims, 3 Drawing Sheets

(56) References Cited

U.S. PATENT DOCUMENTS

| | | | | |
|---|---|---|---|---|
| 2002/0188199 | A1* | 12/2002 | McLaughlin | G01S 7/52077 600/437 |
| 2004/0236222 | A1* | 11/2004 | Mao | A61B 8/481 600/458 |
| 2005/0004461 | A1* | 1/2005 | Abend | G01S 7/52026 600/437 |
| 2005/0228282 | A1* | 10/2005 | Wang | A61B 8/00 600/453 |
| 2005/0277835 | A1* | 12/2005 | Angelsen | A61B 8/14 600/437 |
| 2006/0052699 | A1* | 3/2006 | Angelsen | A61B 8/14 600/437 |
| 2009/0024036 | A1* | 1/2009 | Pan | A61B 8/481 600/447 |
| 2010/0298709 | A1* | 11/2010 | Needles | A61B 8/06 600/458 |
| 2012/0010560 | A1* | 1/2012 | Kadzlauskas | A61F 9/00745 604/22 |
| 2014/0336513 | A1 | 11/2014 | Sang et al. | |
| 2016/0131749 | A1* | 5/2016 | Kim | G01S 7/52074 367/7 |
| 2016/0206282 | A1* | 7/2016 | Kim | G01S 15/8925 |

* cited by examiner

METHOD AND ULTRASOUND SYSTEM FOR FORMING CONTRAST PULSE SEQUENCE ULTRASOUND IMAGE

TECHNICAL FIELD

The present disclosure relates to a method and an ultrasound system for forming a contrast pulse sequence ultrasound image using a pulse width modulation method.

BACKGROUND ART

An ultrasound system has non-invasive and non-destructive characteristics, and thus is widely used in medical fields to obtain information on the interior of a target object. The ultrasound system can provide high-resolution images of the interior of the target object in real time without having to conduct a surgical operation in which the target object is directly incised and observed. Thus, the ultrasound system is quite importantly used in the medical field.

An ultrasound system generates ultrasound data by transmitting an ultrasound signal to a target object, receiving an ultrasound echo signal reflected from the target object, and performing signal processing on the received ultrasound echo signal. Furthermore, the ultrasound system performs scan conversion or rendering processing on the ultrasound data to form an ultrasound image.

A contrast agent may be used to enable a user to more clearly observe an ultrasound image of a region of interest (ROI) of a target object. In this case, after the contrast agent is administered to the subject, a contrast ultrasound image is formed using an ultrasound system. For example, the contrast agent used in forming an ultrasound image includes fine particles containing a gas such as micro-bubbles or the like. As a method for forming the contrast ultrasound image, a contrast pulse sequence (CPS) method can be used. In the contrast pulse sequence method, echo signals corresponding to a plurality of pulses are synthesized to enhance the contrast of the ultrasound image by suppressing a linear component and maximizing a non-linear component originated from micro-bubbles.

Examples of the contrast pulse sequence method include an amplitude modulation method in which a linear component contained in the echo signals is suppressed by modulating the amplitude of a plurality of pulses, and an element masking method in which a linear component contained in the echo signals is suppressed by changing an aperture of a piezoelectric element which activates ultrasound signals corresponding to a plurality of pulses for transmitting the ultrasound signals to the target object.

DISCLOSURE OF INVENTION

Technical Task

When the amplitude modulation method is used to form a contrast pulse sequence ultrasound image, it is necessary for an ultrasound system to generate power corresponding to the modulated amplitude. Thus, there is a need to use a dual power system or a power system capable of generating a plurality of power levels two or more levels. As a result, the configuration of the ultrasound system may become complex, and the associated cost may increase. In contrast, when the element masking method is used, the ultrasound system may be realized as a single power system. However, according to the element masking method, an image artifact may be generated in the contrast pulse sequence ultrasound image.

Technical Solution

According to one embodiment of the present disclosure, a method for forming a contrast pulse sequence ultrasound image includes: generating at least three kinds of mutually different pulses having a same amplitude; sequentially transmitting at least three kinds of transmission signals corresponding to the at least three kinds of mutually different pulses to an ultrasound transducer; transmitting, by the ultrasound transducer, at least three kinds of ultrasound signals to a target object by sequentially generating the at least three kinds of ultrasound signals based on the at least three kinds of transmission signals; generating, by the ultrasound transducer, at least three kinds of reception signals by sequentially receiving at least three kinds of echo signals reflected from the target object; and forming the contrast pulse sequence ultrasound image by eliminating a linear component from the at least three kinds of reception signals.

In the method according to one embodiment of the present disclosure, generating the at least three kinds of mutually different pulses may include: generating a first pulse having a pulse width corresponding to one half of a predetermined pulse width; generating a second pulse having the predetermined pulse width and having a delayed phase difference of 180 degrees with respect to the predetermined pulse; and generating a third pulse having the same pulse width as the first pulse and having a delayed phase difference of 90 degrees with respect to the first pulse.

In the method according to one embodiment of the present disclosure, forming the contrast pulse sequence ultrasound image may include forming the contrast pulse sequence ultrasound image including a non-linear component by eliminating the linear component from the at least three kinds of reception signals and synthesizing the at least three kinds of reception signals.

In the method according to one embodiment of the present disclosure, generating the at least three kinds of mutually different pulses may include generating the at least three kinds of mutually different pulses having the same amplitude using one power source.

In the method according to one embodiment of the present disclosure, the non-linear component may include a plurality of non-linear components including at least one non-linear component of one or more even number orders and at least one non-linear component of one or more odd number orders.

According to another embodiment of the present disclosure, a computer-readable storage medium stores a program configured to, when executed, perform the contrast pulse sequence ultrasound image forming method.

According to a further embodiment of the present disclosure, an ultrasound system includes: a processing unit configured to generate at least three kinds of mutually different pulses having a same amplitude and to generate at least three kinds of transmission signals corresponding to the at least three kinds of mutually different pulses; and an ultrasound transducer configured to sequentially generate at least three kinds of ultrasound signals based on the at least three kinds of transmission signals, transmit the at least three kinds of ultrasound signals to a target object, sequentially receive at least three kinds of echo signals reflected from the target object, and generate at least three kinds of reception signals, wherein the processing unit is configured to form a contrast pulse sequence ultrasound image by removing a linear component from the at least three kinds of reception signals.

In the system according to a further embodiment of the present disclosure, the processing unit may be configured to generate a first pulse having a pulse width corresponding to one half of a predetermined pulse width, a second pulse having the predetermined pulse width and having a delayed phase difference of 180 degrees with respect to the predetermined pulse, and a third pulse having the same pulse width as the first pulse and having a delayed phase difference of 90 degrees with respect to the first pulse.

In the system according to a further embodiment of the present disclosure, the processing unit may be configured to form the contrast pulse sequence ultrasound image including a non-linear component by eliminating the linear component from the at least three kinds of reception signals and synthesizing the at least three kinds of reception signals.

In the system according to a further embodiment of the present disclosure, the processing unit may be configured to generate the at least three kinds of mutually different pulses having the same amplitude based on one power source.

In the system according to a further embodiment of the present disclosure, the at least three kinds of mutually different pulses may include the first to third pulses and the at least three kinds of reception signals may include first to third reception signals. Further, the processing unit may be configured to form the contrast pulse sequence ultrasound image by synthesizing the first to third reception signals.

In the system according to a further embodiment of the present disclosure, the non-linear component may include a plurality of non-linear components including at least one non-linear component of one or more even number orders and at least one non-linear component of one or more odd number orders.

Advantageous Effect

According to some embodiments of the present disclosure, by forming contrast pulse sequence ultrasound images using the pulse width modulation method, the ultrasound system may be realized using a low-priced power system having a relatively simple structure, such as a single power system or the like. In addition, it may be possible to form a contrast pulse sequence ultrasound image with reduced image artifacts than an ultrasound image formed using an element masking method.

DETAILED DESCRIPTION

Some embodiments of the present disclosure will now be described in detail with reference to the accompanying exemplary drawings. The term "unit" used herein refers to software or hardware such as an FPGA (field-programmable gate array), an ASIC (application specific integrated circuit), or the like. However, the "unit" is not limited to software or hardware. The "unit" may be configured to exist in an addressable storage medium or may be configured to reproduce one or more processors. Accordingly, as one example, the term "unit" may include components such as software components, object-oriented software components, class components, task components or the like as well as a processor, a function, an attribute, a procedure, a subroutine, a segment of a program code, a driver, firmware, a microcode, a circuit, data, a database, a data structure, a table, an array and a variable. The functions provided within a component and the "unit" may be combined into a smaller number of components and "units" or may be divided into additional components and "units."

Figure 1:
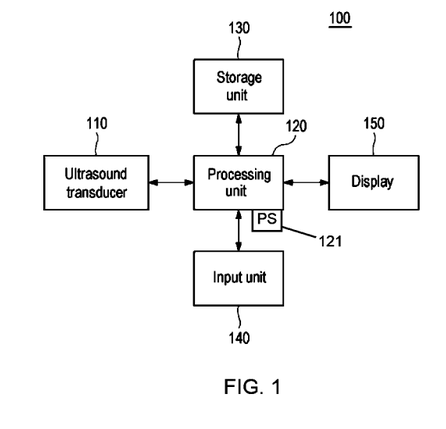
FIG. 1 is a block diagram illustrating a configuration of an ultrasound system according to one embodiment of the present disclosure.

FIG. 1 is a block diagram illustrating a configuration of an ultrasound system according to one embodiment of the present disclosure.

As illustrated in FIG. 1, an ultrasound system 100 may include an ultrasound transducer 110, a processing unit 120, a storage unit 130, an input unit 140, and a display 150.

The ultrasound transducer 110 may convert an electrical signal to an ultrasound signal or vice versa. The ultrasound transducer 110 is a sensor used to obtain clinical information such as spatial information, an anatomical shape, or the like of a target object, by transmitting ultrasound signals to the target object, receiving ultrasound signals (or echo signals) reflected from the target object, and providing electrical signals corresponding to the received ultrasound signals to the ultrasound system 100. In the present disclosure, the term "ultrasound transducer" may be used in the same meaning as an ultrasound probe or the like and may include, for example, a convex transducer, a linear transducer and the like. However, the ultrasound transducer is not limited thereto. The ultrasound transducer 110 may include a plurality of piezoelectric elements (not shown) which operates to interconvert electrical signals and ultrasound signals. The ultrasound transducer 110 may transmit ultrasound signals to the target object in response to electrical signals (transmission signals) inputted to the piezoelectric elements. The target object may be a living body (e.g., a body portion or an organ of a human, including a blood vessel, a heart, a liver, or the like) to which a contrast agent is administered. Further, in the case of receiving echo signals reflected from the target object which receives the ultrasound signals, the ultrasound transducer 110 may convert the received echo signals to electrical signals (hereinafter referred to as a "reception signal"). In one embodiment, the ultrasound transducer 110 may sequentially output a plurality of ultrasound signals in response to transmission signals corresponding to a plurality of pulses transmitted from the processing unit 120. In one embodiment, the ultrasound transducer 110 may form a first ultrasound signal in response to a first transmission signal received from the processing unit 120 and may transmit the first ultrasound signal to the target object. Furthermore, the ultrasound transducer 110 may form a second ultrasound signal in response to a second transmission signal received from the processing unit 120 and may transmit the second ultrasound signal to the target object. In addition, the ultrasound transducer 110 may form a third ultrasound signal in response to a third transmission signal received from the processing unit 120 and may transmit the third ultrasound signal to the target object. Further, the ultrasound transducer 110 may receive a plurality of echo signals sequentially reflected from the target object sequentially receiving the transmitted ultrasound signals and may sequentially convert the received echo signals to a plurality of reception signals. In one embodiment, the ultrasound transducer 110 may convert a first echo signal received from the target object receiving the first ultrasound signal to a first reception signal. Furthermore, the ultrasound transducer 110 may convert a second echo signal received from the target object receiving the second ultrasound signal to a second reception signal. Moreover, the ultrasound transducer 110 may convert a third echo signal received from the target object receiving the third ultrasound signal to a third reception signal.

The processing unit 120 may form at least three kinds of mutually different pulses having a same amplitude. In one embodiment, the processing unit 120 may form at least three kinds of mutually different pulses having an amplitude of equal level based on one power source 121. Furthermore, the processing unit 120 may amplify the power of at least three kinds of mutually different pulses having the same amplitude to a same level and form transmission signals corresponding to the at least three kinds of pulses. The processing unit 120 may transmit the at least three kinds of transmission signals to a plurality of piezoelectric elements of the ultrasound transducer 110.

Figure 2:
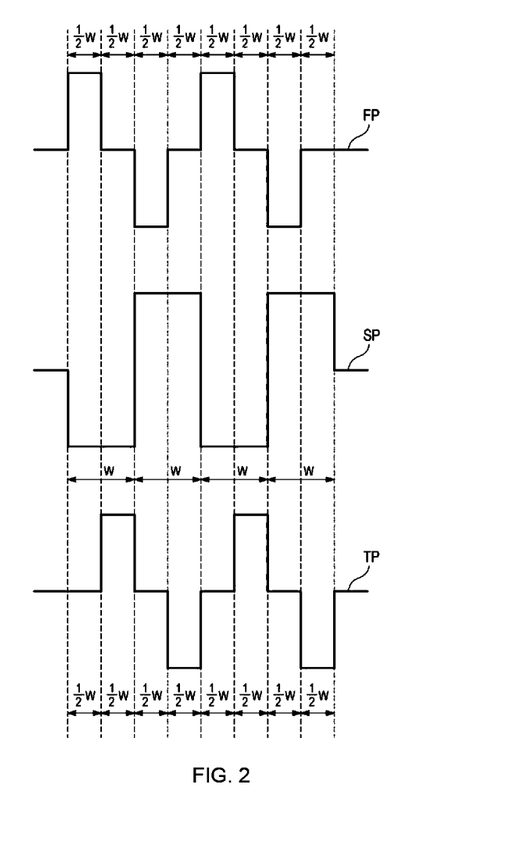
FIG. 2 is an exemplary timing diagram of a first, second, and third pulses generated by an ultrasound system according to one embodiment of the present disclosure.

In one embodiment, as illustrated in FIG. 2, the processing unit 120 generates a first pulse FP having a pulse width corresponding to one half of a predetermined pulse width w and generates a first transmission signal corresponding to the first pulse FP by amplifying the power of the first pulse FP to a predetermined level. Further, the processing unit 120 generates a second pulse SP having the predetermined pulse width and having a delayed phase difference of 180 degrees with respect to the predetermined pulse and generates a second transmission signal corresponding to the second pulse SP by amplifying the power of the second pulse SP to the predetermined level. In addition, the processing unit 120 generates a third pulse TP having the same pulse width as the first pulse FP and having a delayed phase difference of 90 degrees with respect to the first pulse FP and generates a third transmission signal corresponding to the third pulse TP by amplifying the power of the third pulse TP to the predetermined level. The at least three kinds of pulses generated in the processing unit 120 have an amplitude of equal level. The ultrasound system 100 may be configured to use a power system capable of generating single power for amplifying the at least three kinds of pulses, which were formed by the processing unit 120 to have an amplitude of the same level, to a predetermined level corresponding to the amplitude of the associated level. Thus, the ultrasound system 100 can be configured more simply and economically than an ultrasound system using an amplitude modulation method, which has to be configured with a dual power or a power system capable of generating a plurality of power levels two or more levels.

The processing unit 120 applies a delay to each of the first to third transmission signals in view of the distance between the focal point on which the ultrasound signal is focused within the target object and the respective piezoelectric elements of the ultrasound transducer 110. The processing unit 120 then sequentially transmits the delayed first to third transmission signals to the ultrasound transducer 110. Based on the first to third transmission signals, the ultrasound transducer 110 transmits the first to third ultrasound signals to the target object and receives the first to third echo signals sequentially reflected from the target object. The ultrasound transducer 110 sequentially converts the received first to third echo signals to form the first to third reception signals. Further, the processing unit 120 may generate ultrasound data of the target object by synthesizing the first to third reception signals provided from the ultrasound transducer 110 and eliminating a linear component from the first to third reception signals in the synthesizing process. That is, when synthesizing the first to third reception signals corresponding to the first to third pulses FP, SP, and TP, the processing unit 120 may eliminate a linear component contained in the first to third reception signals so that a non-linear component of the first to third reception signals is included in the ultrasound data. The linear component included in the first to third reception signals may be formed by bodily tissue of the target object and the non-linear component may be formed by the contrast agent (micro-bubbles). For example, if the target object is a portion of a human body comprising a homogeneous tissue, the echo signal reflected from the target object in response to the transmission signals transmitted from the ultrasound transducer 110 may contain a linear component. On the other hand, since the contrast agent includes bubbles, each of which is surrounded by a thin film containing a gas, the transmission signals transmitted from the ultrasound transducer 110 may be irregularly reflected due to the interaction of the gas and the thin film. As a result, an echo signal reflected by the target object administered with the contrast agent may contain a non-linear component. If the first to third reception signals are expressed in the form of harmonic waves, the linear component may contain a primary harmonic wave. The non-linear component may include at least one harmonic wave of one or more even number orders and at least one harmonic wave of one or more odd number orders. That is, the non-linear component may include one or more harmonic waves higher than the primary harmonic wave.

The processing unit 120 may form an ultrasound image of the target object using the ultrasound data. The ultrasound image may include a contrast pulse sequence ultrasound image formed using a contrast pulse sequence method.

The storage unit 130 may store the ultrasound data formed in the processing unit 120. Further, the storage unit 130 may store ultrasound images of the target object formed in the processing unit 120. As one example, the storage unit 130 may include, but is not limited to, a hard disk, a nonvolatile memory, a CD-ROM (Compact Disc-Read Only Memory), a DVD-ROM (Digital Versatile Disc-Read Only Memory), and the like.

The input unit 140 may receive input information inputted by a user. The input information may include information for selecting one ultrasound transducer 110 from a plurality of ultrasound transducers included in the ultrasound system 100, information for generating the first to third pulses, etc. Herein, the information for generating the first to third pulses may include information for adjusting the pulse width and the phase difference of the respective pulses. For example, the information for generating the first to third pulses may include information for forming the first pulse having a pulse width corresponding to one half of a predetermined pulse width pre-set in the ultrasound system 100, the second pulse having a pulse width equal to the predetermined pulse width and having a delayed phase difference of 180 degrees with respect to the predetermined pulse, and the third pulse having a pulse width equal to the pulse width of the first pulse and having a delayed phase difference of 90 degrees with respect to the first pulse. In one embodiment, the input unit 140 may include, but is not limited to, a control panel, a track ball, a keyboard, a mouse, a touch screen, and the like.

The display 150 may display ultrasound images of the target object formed by the processing unit 120. Further, the display 150 may display the input information received from the input unit 140. The display 150 may include, but is not limited to, an LCD (Liquid Crystal Display), an LED (Light Emitting Diode) display, an OLED (Organic Light Emitting Diode) display, and the like.

Figure 3:
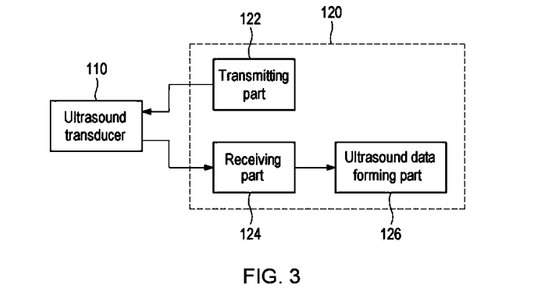
FIG. 3 is a block diagram illustrating a configuration of a processing unit according to one embodiment of the present disclosure.

FIG. 3 is a block diagram illustrating a configuration of the processing unit according to one embodiment of the present disclosure.

As illustrated in FIG. 3, the processing unit 120 may include a transmitting part 122, a receiving part 124, and an ultrasound data forming part 126.

The transmitting part 122 transmits one or more transmission signals to the ultrasound transducer 110, thereby controlling the transmission of the ultrasound signal performed by the ultrasound transducer 110. Further, the transmitting part 122 generates at least three kinds of mutually different pulses having the same amplitude and generates transmission signals corresponding to the at least three kinds of pulses for obtaining an ultrasound image. In one embodiment, the transmitting part 122 may generate the first to third pulses FP, SP, and TP illustrated in FIG. 2 and generate the first to third transmission signals corresponding to the first to third pulses FP, SP, and TP. Accordingly, the ultrasound transducer 110 converts the transmission signals supplied from the transmitting part 122 to ultrasound signals, transmits the converted ultrasound signals to the target object, receives echo signals reflected from the target object, and generates reception signals. In one embodiment, the ultrasound transducer 110 may convert the first to third transmission signals to the first to third ultrasound signals, transmit the converted first to third ultrasound signals to the target object, receive the first to third echo signals reflected from the target object, and generate the first to third reception signals.

The receiving part 124 generates digital signals by performing analog-to-digital conversion of the reception signals supplied from the ultrasound transducer 110 and generates receive-focused signals by performing receive beamforming on the digital signals. In one embodiment, the receiving part 124 may convert the first to third reception signals supplied from the ultrasound transducer 110 to first to third digital signals, respectively, and generate first to third receive-focused signals by performing receive beamforming on the first to third digital signals, respectively.

The ultrasound data forming part 126 may synthesize the receive-focused signals provided from the receiving part 124 and eliminate a linear component contained in the receive-focused signals during the synthesis process. In one embodiment, the ultrasound data forming part 126 may synthesize the first to third receive-focused signals provided from the receiving part 124 and generate synthesized receive-focused signals from which the linear components included in the first to third receive-focused signals are eliminated. Further, the ultrasound data forming part 126 may form ultrasound data by performing various types of signal processing (e.g., a low path filtering, gain adjustment, scan conversion, or the like) with respect to the synthesized receive-focused signals. The ultrasound data may include, but are not limited to, RF (radio frequency) data or IQ (in-phase/quadrature) data.

Figure 4:
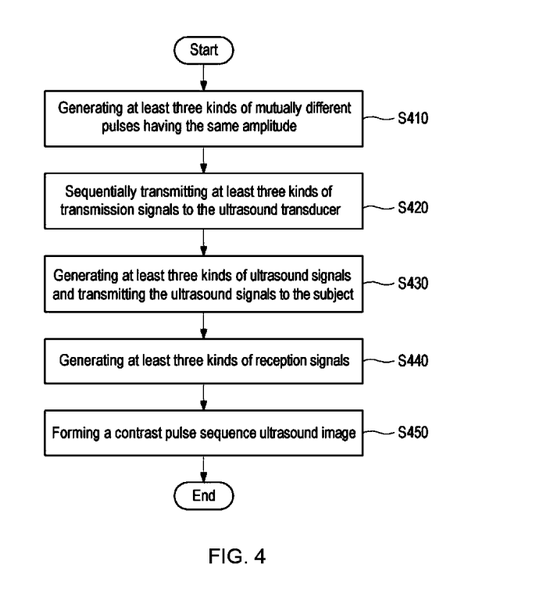
FIG. 4 is a flowchart illustrating a method for forming a contrast pulse sequence ultrasound image according to one embodiment of the present disclosure.

FIG. 4 is a flowchart illustrating a method of forming a contrast pulse sequence ultrasound image according to one embodiment of the present disclosure. In this flowchart, process steps, method steps or algorithms are illustrated in a sequential order. However, the process steps, the method steps or the algorithms may be configured to operate in any arbitrarily suitable order. In other words, the arbitrary sequence or order of steps described in the present disclosure does not mean that the steps must be performed in that order. Furthermore, although some steps of the flowchart are described and illustrated as being performed non-simultaneously, such steps may be performed simultaneously. In addition, the illustration of a process depicted in the drawings does not mean that the illustrated process excludes other changes and modifications thereof. Further, the illustration of a process or an arbitrary step thereof does not mean that the illustrated process or arbitrary step is essential in the present disclosure and that the illustrated process is preferred.

As illustrated in FIG. 4, at step S410, at least three kinds of mutually different pulses having the same amplitude are generated. For example, referring to FIGS. 1 to 3, the ultrasound system 100 generates the first pulse FP having a pulse width corresponding to one half of the predetermined pulse width w as illustrated in FIG. 2. In addition, the ultrasound system 100 generates the second pulse SP having the predetermined pulse width and having a phase delay difference of 180 degrees with respect to the predetermined pulse. Further, the ultrasound system 100 generates the third pulse TP having the same pulse width as the first pulse FP and having a phase delay difference of 90 degrees with respect to the first pulse FP.

At step S420, at least three kinds of transmission signals corresponding to the at least three kinds of pulses are sequentially transmitted to the ultrasound transducer 110. For example, referring to FIGS. 1 to 3, the ultrasound system 100 generates the first transmission signal by amplifying the power of the first pulse FP to a predetermined level so as to correspond to the amplitude of the first pulse FP as illustrated in FIG. 2. After delaying the first transmission signal in view of the distance between the focal point and the respective piezoelectric elements of the ultrasound transducer 110, the ultrasound system 100 transmits the delayed first transmission signal to the ultrasound transducer 110. Further, the ultrasound system 100 generates the second transmission signal by amplifying the power of the second pulse SP to the predetermined level so as to correspond to the amplitude of the second pulse SP. After delaying the second transmission signal in view of the distance between the focal point and the respective piezoelectric elements of the ultrasound transducer 110, the ultrasound system 100 transmits the delayed second transmission signal to the ultrasound transducer 110. Additionally, the ultrasound system 100 generates the third transmission signal by amplifying the power of the third pulse TP to the predetermined level so as to correspond to the amplitude of the third pulse TP. After delaying the third transmission signal in view of the distance between the focal point and the respective piezoelectric elements of the ultrasound transducer 110, the ultrasound system 100 transmits the delayed third transmission signal to the ultrasound transducer 110.

At step S430, based on the at least three kinds of the transmission signals, the ultrasound transducer 110 sequentially generates at least three kinds of ultrasound signals and transmits the at least three kinds of ultrasound signals to the target object. For example, referring to FIGS. 1 to 3, the ultrasound transducer 110 generates a first ultrasound signal in response to the received first transmission signal and transmits the first ultrasound signal to the target object. Additionally, the ultrasound transducer 110 generates a second ultrasound signal in response to the received second transmission signal and transmits the second ultrasound signal to the target object. Further, the ultrasound transducer 110 generates a third ultrasound signal in response to the received third transmission signal and transmits the third ultrasound signal to the target object.

At step S440, the ultrasound transducer 110 sequentially receives at least three kinds of echo signals reflected from the target object and generates at least three kinds of reception signals. For example, referring to FIGS. 1 to 3, the ultrasound transducer 110 converts the first echo signal, which is received from the target object in response to the first ultrasound signal, to the first reception signal. Further, the ultrasound transducer 110 converts the second echo signal, which is received from the target object in response to the second ultrasound signal, to the second reception signal. Additionally, the ultrasound transducer 110 converts the third echo signal, which is received from the target object in response to the third ultrasound signal, to the third reception signal.

At step S450, a contrast pulse sequence ultrasound image may be formed by eliminating linear components from the at least three kinds of reception signals. For example, referring to FIGS. 1 to 3, the ultrasound system 100 may form ultrasound data of the target object by synthesizing the first to third reception signals provided from the ultrasound transducer 110 and eliminating linear components from the first to third reception signals during the synthesis process. That is, when synthesizing the first to third reception signals corresponding to the first to third pulses FP, SP, and TP, the ultrasound system 100 may eliminate the linear components contained in the first to third reception signals so that the non-linear components contained in the first to third reception signals are included in the ultrasound data. In addition, the ultrasound system 100 may form a contrast pulse sequence ultrasound image of the target object by performing a scan conversion or rendering process on the ultrasound data of the target object.

While the aforementioned method has been described using specific embodiments, it may be possible to realize the aforementioned method as computer-readable codes stored in a computer-readable recording medium. The computer-readable recording medium may include all kinds of recording devices which store data readable by a computer system. Examples of the computer-readable recording medium include a ROM, a RAM, a CD-ROM, a magnetic tape, a floppy disk, an optical data storage device, and the like. The computer-readable recording medium may be realized in the form of a carrier wave (e.g., a transmission through the Internet). Furthermore, the computer-readable recording medium may be dispersed in computer systems connected by a network. Computer-readable codes may be stored and executed in a dispersed manner. Functional programs, codes, and code segments for realizing the aforementioned embodiments may be easily inferred by programmers in the technical field to which the present disclosure pertains.

While certain embodiments have been described, these embodiments have been presented by way of example only, and are not intended to limit the scope of the disclosures. Indeed, the embodiments described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

We claim:

1. A method for forming a contrast pulse sequence ultrasound image, comprising:

generating at least three mutually different pulses having a same amplitude and a same frequency with differences in both pulse width and phasing, wherein generating the at least three mutually different pulses comprises: generating a first pulse having a pulse width corresponding to one half of a predetermined pulse width, generating a second pulse having the predetermined pulse width and having a delayed phase difference of 180 degrees with respect to the first pulse, and generating a third pulse having a same pulse width as the first pulse and having a delayed phase difference of 90 degrees with respect to the first pulse;

sequentially transmitting at least three transmission signals corresponding to the at least three mutually different pulses to an ultrasound transducer;

transmitting, by the ultrasound transducer, at least three ultrasound signals to a target object by sequentially generating the at least three ultrasound signals based on the at least three transmission signals;

generating, by the ultrasound transducer, at least three reception signals by sequentially receiving at least three echo signals reflected from the target object; and forming the contrast pulse sequence ultrasound image by eliminating a linear component from the at least three reception signals.

2. The method of claim 1, wherein by eliminating the linear component from the at least three reception signals, the contrast pulse sequence ultrasound image includes a non-linear component and wherein forming the contrast pulse sequence ultrasound image further comprises synthesizing the at least three reception signals forming.

3. The method of claim 2, wherein the non-linear component comprises a plurality of non-linear components including at least one non-linear component of one or more even number orders and at least one non-linear component of one or more odd number orders.

4. The method of claim 1, wherein generating the at least three mutually different pulses comprises:

generating the at least three mutually different pulses having the same amplitude using one power source.

5. The method of claim 1, wherein the at least three mutually different pulses include the first to third pulses, the at least three reception signals include first to third reception signals, and forming the contrast pulse sequence ultrasound image includes forming the contrast pulse sequence ultrasound image by synthesizing the first to third reception signals.

6. An ultrasound system, comprising:

a processing unit configured to generate at least three mutually different pulses having a same amplitude and a same period with differences in both pulse width and phasing and to generate at least three transmission signals corresponding to the at least three mutually different pulses, wherein the processing unit is configured to generate a first pulse having a pulse width corresponding to one half of a predetermined pulse width, a second pulse having the predetermined pulse width and having a delayed phase difference of 180 degrees with respect to the first pulse, and a third pulse having a same pulse width as the first pulse and having a delayed phase difference of 90 degrees with respect to the first pulse; and an ultrasound transducer configured to sequentially generate at least three ultrasound signals based on the at least three transmission signals and transmit the at least three ultrasound signals to a target object, the ultrasound transducer being further configured to sequentially receive at least three echo signals reflected from the target object and generate at least three reception signals, wherein the processing unit is configured to form a contrast pulse sequence ultrasound image by removing a linear component from the at least three reception signals.

7. The system of claim 6, wherein by eliminating the linear component from the at least three reception signals, the contrast pulse sequence ultrasound image includes a non-linear component, and wherein the processing unit is configured to synthesize the at least three reception signals.

8. The system of claim 7, wherein the non-linear component comprises a plurality of non-linear components including at least one non-linear component of an even number order and at least one non-linear component of an odd number order.

9. The system of claim 6, wherein the processing unit is configured to generate the at least three mutually different pulses having the same amplitude using one power source.

10. The system of claim 6, wherein the at least three mutually different pulses include the first to third pulses, the at least three reception signals include first to third reception signals, and the processing unit is configured to form the contrast pulse sequence ultrasound image by synthesizing the first to third reception signals.

\* \* \* \* \*